United States Patent  
Tsukada et al.

(10) Patent No.: US 6,172,501 B1
(45) Date of Patent: Jan. 9, 2001

(54) METHOD AND APPARATUS FOR MEASURING THE DEGREE OF CABLE CORROSION

(75) Inventors: Kazuhiko Tsukada, Kyoto; Toshiyuki Moriya, Tokyo, both of (JP)

(73) Assignee: Tokyo Rope Mfg. Co., Ltd., Tokyo (JP)

(*) Notice: Under 35 U.S.C. 154(b), the term of this patent shall be extended for 0 days.

(21) Appl. No.: 09/474,780

(22) Filed: Dec. 30, 1999

Related U.S. Application Data

(62) Division of application No. 08/885,689, filed on Jun. 30, 1997.

(30) Foreign Application Priority Data

Jun. 28, 1996 (JP) .................................................. 8-186974

(51) Int. Cl.[7] .................................................. G01N 27/82
(52) U.S. Cl. ........................... 324/227; 324/232; 324/242
(58) Field of Search .................................. 324/227, 225, 324/226, 228, 229, 232–235, 236–243, 262; 335/284

(56) References Cited

U.S. PATENT DOCUMENTS

| | | | |
|---|---|---|---|
| 2,895,103 | 7/1959 | Vogt et al. | 324/260 |
| 4,598,250 | 7/1986 | Lorenzi et al. | 324/220 |
| 4,611,170 | 9/1986 | Stanley et al. | 324/229 |
| 4,652,823 | 3/1987 | Sutton | 324/240 |
| 4,827,215 | 5/1989 | van der Walt | 324/227 |
| 5,036,277 | 7/1991 | van der Walt | 324/235 |
| 5,237,270 | 8/1993 | Cecco et al. | 324/220 |
| 5,245,279 | 9/1993 | Bendzsak | 324/225 |
| 5,414,353 | 5/1995 | Weischedel | 324/232 |
| 5,446,382 | 8/1995 | Flora | 324/232 |
| 5,473,247 | 12/1995 | You et al. | 324/227 |

FOREIGN PATENT DOCUMENTS

| | | |
|---|---|---|
| 913780 | 12/1962 | (GB). |
| 1270748 | 4/1972 | (GB). |
| 2012966 | 8/1979 | (GB). |
| 50-43958 | 4/1975 | (JP). |
| 63-11852 | 1/1988 | (JP). |
| 3-262958 | 11/1991 | (JP). |

*Primary Examiner*—Jay Patidar
(74) *Attorney, Agent, or Firm*—Morrison & Foerster LLP

(57) ABSTRACT

A detecting coil device mounted on part of a cable to evaluate the degree of corrosion of the cable, which is used, for example, on suspension or skew bridges. The detecting coil device is provided with a detecting coil and Hall elements. A magnetizer having a magnetizing coil is mounted as to enclose the cable and the detecting coil device. When current flows through the magnetizing coil, it magnetizes the cable. The magnetic field strength is detected by the Hall element, and the amount of magnetic flux passing through the cable is detected using the detecting coil. The cross-sectional area of the cable is also calculated on the basis of the magnetic field strength and the amount of magnetic flux which are detected and the permeability of the cable. The degree at which the cross-sectional area of the cable is decreased (the corrosion degree) is evaluated by comparing the calculated cross-sectional area of the cable with the cross-sectional area of a reference cable.

11 Claims, 8 Drawing Sheets

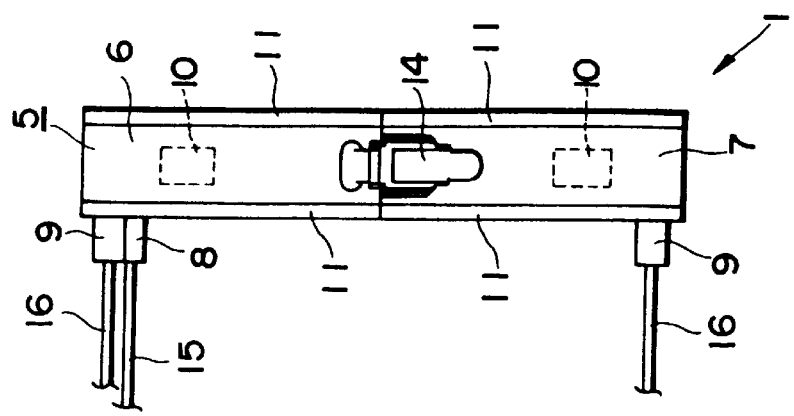
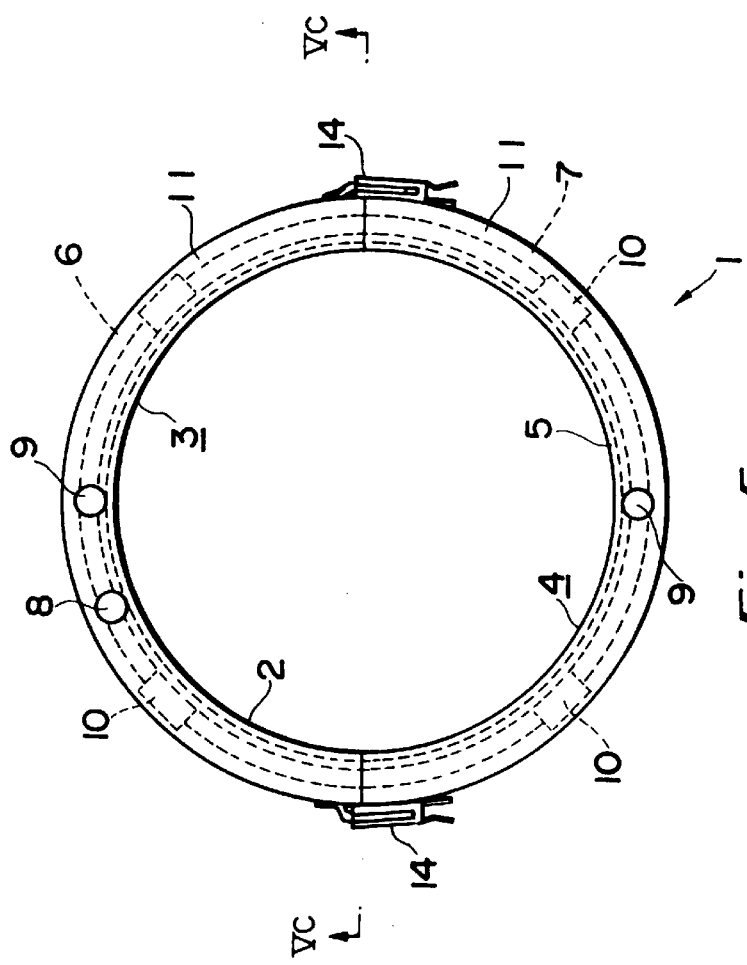
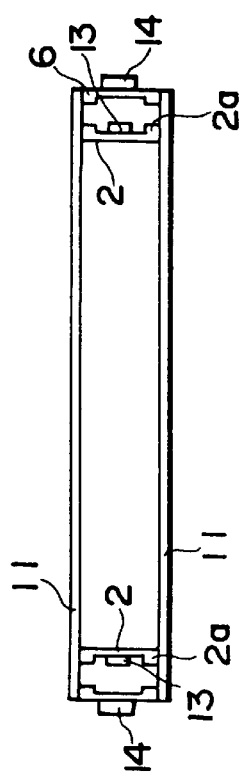

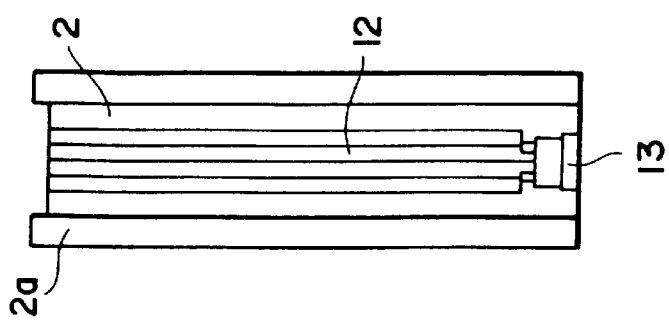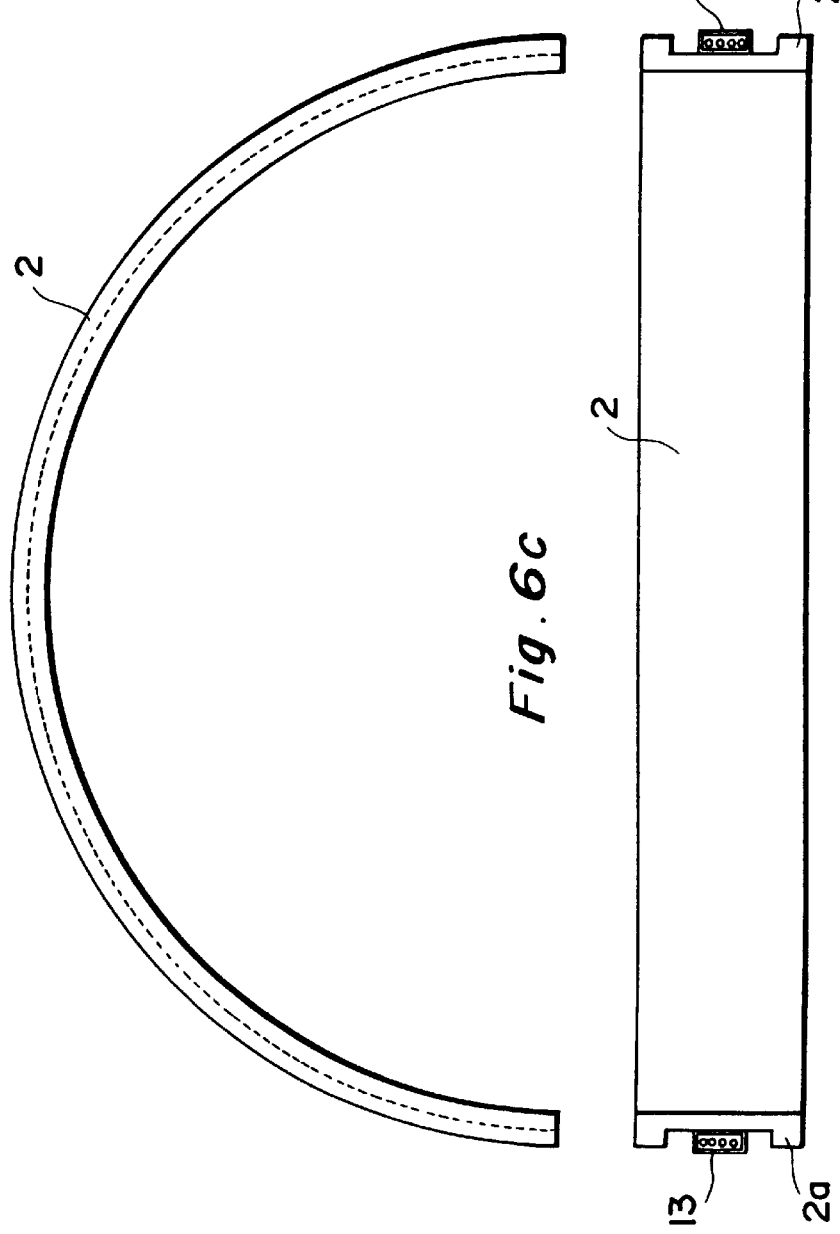

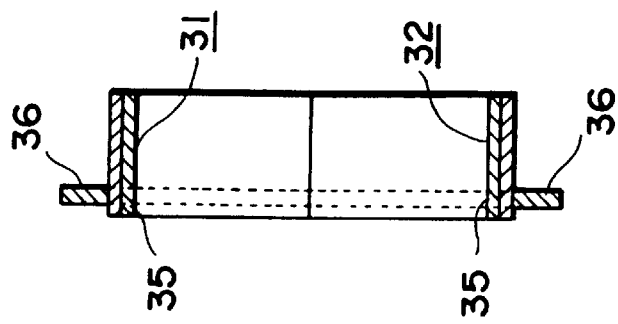
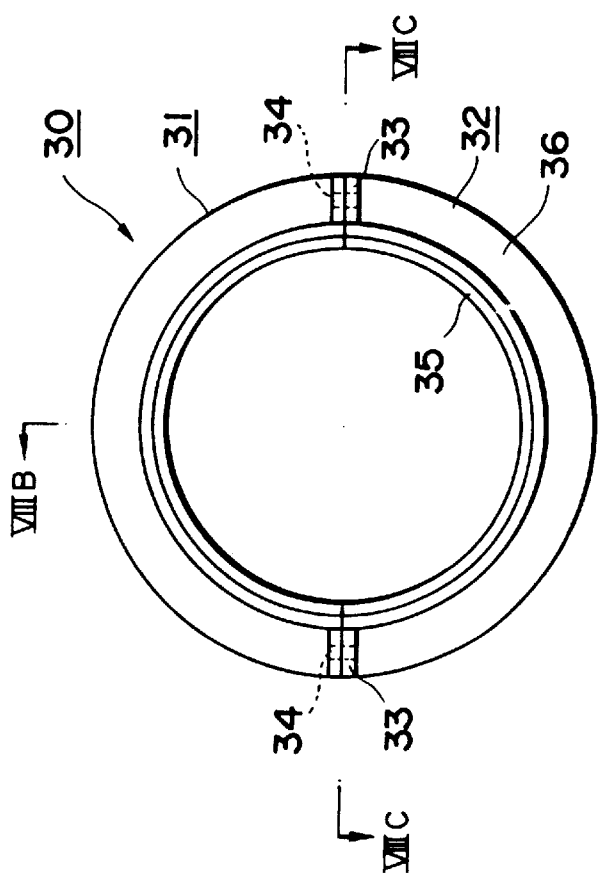
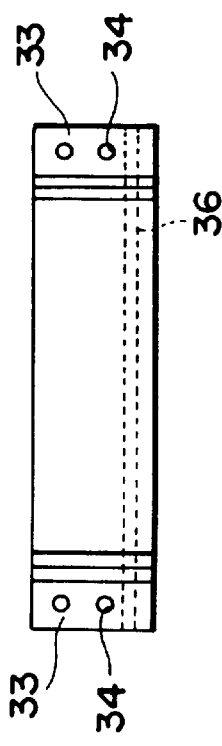

METHOD AND APPARATUS FOR MEASURING THE DEGREE OF CABLE CORROSION

This application is a divisional of Ser. No. 08/885,689 filed Jun. 30, 1997.

BACKGROUND OF THE INVENTION

1. Field of the Invention

The present invention relates to a method of and an apparatus for detecting a corrosion degree of a cable made of ferromagnetic materials (e.g., steel) used for, for example, a suspension bridge, a skew bridge.

The term "cable" includes not only a so-called cable made of ferromagnetic materials but also cable-shaped members such as a rope, strand, code, line, wire, thread, string, stick, rod, pole, staff, club, bar, shaft and the like all of which are made of ferromagnetic materials, irrespective of diameters thereof and shapes of the cross section thereof, and further includes a cable comprising line members which are neither twisted nor braided together but just bundled together as well as a twisted cable, throughout the specification and the appended claims.

2. Background Art

A cable made of a metal (particularly, steel) used for a suspension bridge, a skew bridge, and the like is exposed to the weather because it is outdoors. Further, it is affected by salt water in the neighborhood of the seashore, and is affected by sulfurous acid in an industrial area. Therefore, the cable is not immune to corrosion.

The corrosion degree of the cable has been generally evaluated as follows.

With respect to a cable having a diameter of 60 [mm] or less, the damage of the cable has been detected by a magnetic leakage flux testing. In this method, the local damage such as breaking can be detected, but the entire corrosion cannot be evaluated.

With respect to a cable having a diameter exceeding 60 [mm], the appearance of the cable has been viewed, to evaluate the corrosion degree of the cable. In this method, the precision in the evaluation of the corrosion degree of the cable is low.

There is an apparatus for evaluating the corrosion degree of a cable utilizing a so-called total flux method. The apparatus is forced to be increased in size, and its magnetized state varies depending on the measuring environment, whereby the precision may, in some cases, be decreased.

SUMMARY OF THE INVENTION

An object of the present invention is to provide a method and an apparatus in which the corrosion degree of a cable can be evaluated without making the apparatus relatively large in size and with relatively high precision.

A method of measuring a corrosion degree of a cable according to the present invention comprises the steps of magnetizing an object cable of measurement whose corrosion degree is to be measured, detecting strength of a magnetic field (or magnetic field intensity) for magnetizing the object cable of measurement, detecting an amount of (or quantity of)(or total) magnetic flux passing through the magnetized object cable of measurement, calculating a value relating to a cross-sectional area of the object cable of measurement on the basis of the detected magnetic field strength, the detected amount of magnetic flux, and permeability of the object cable of measurement, and measuring a degree of corrosion of the object cable of measurement on the basis of comparison between the calculated value relating to the cross-sectional area of the object cable of measurement and a value relating to a cross-sectional area of a reference cable.

The present invention presupposes that the object cable of measurement is a ferromagnetic material. The object cable of measurement is magnetized. Let H be the strength of the magnetic field (or magnetic field intensity) for magnetizing the object cable of measurement. Let be the amount of (or total or main) magnetic flux passing through the magnetized object cable of measurement, and B be the magnetic flux density thereof.

Letting $\mu$ be the permeability of the object cable of measurement, and A be the cross-sectional area of the object cable of measurement, the following equation holds:

$$B = \mu H = \Phi/A \qquad (1)$$

The following equation is obtained by modifying the above equation (1):

$$A = \Phi/\mu H \qquad (2)$$

If the permeability $\mu$ and the magnetic field strength H are considered to be constant, the cross-sectional area A of the object cable of measurement is proportional to the amount of magnetic flux $\Phi$. The degree of corrosion of the object cable of measurement appears in the cross-sectional area A. If there is no corrosion, the cross-sectional area A is generally kept constant. If the corrosion advances, the cross-sectional area A is decreased (a corroded portion can be regarded as a non-magnetic material). By making a comparison between the cross-sectional area of the reference cable and the cross-sectional area of the object cable of measurement, the degree of corrosion of the object cable of measurement can be evaluated.

Examples of the reference cable include an object cable of measurement itself, and a cable of the same material and construction as those of the object cable of measurement. When a new cable is laid or used, the cross-sectional area thereof is measured (this cross-sectional area is taken as an initial cross-sectional area). When a certain time period (for example, one year, five years, ten years, or twenty years) has elapsed since the cable was laid or used, the cross-sectional area of the cable which has been laid or used is measured. If the measured cross-sectional area is compared with the initial cross-sectional area, the degree of corrosion caused in the elapsed time period can be evaluated. When corrosion is checked with respect to a cable which was already provided in the past, a new cable of the same material, construction and size as those of the past cable may be produced as a reference cable.

The use of the value relating to the cross-sectional area is sufficient to evaluate the corrosion degree. The value relating to the cross-sectional area may be the cross-sectional area A itself. Alternatively, it may be a value proportional to the cross-sectional area, the detected amount of magnetic flux $\Phi$, a value proportional to the amount of magnetic flux $\Phi$, and the like.

It is not always necessary to assume that the magnetic field strength H and the permeability $\mu$ are fixed to be a constant. According to the equation (2), if the permeability $\mu$, the magnetic field strength H, and the amount of magnetic flux $\Phi$ are determined, a value relating to the cross-sectional area A is found. Consequently, the magnetic field strength H and the amount of magnetic flux $\Phi$ may be measured. With respect to a cable of the same material as that of the object cable of measurement (the cross-sectional area of which has been known), the permeability $\mu$ can be previously obtained in correspondence with the magnetic field strength H.

A ferromagnetic material generally has magnetic hysteresis characteristics. A method of magnetizing the object cable of measurement (the direction of current, and the directions in which the current is increased and decreased) is fixedly predetermined. Measurements are made in a region where the amount of magnetic flux is uniquely determined or almost uniquely determined with respect to the magnetic field strength. For example, the magnetic field strength and the amount of magnetic flux may be measured in a region where the magnetic field is saturated.

The magnetization of the object cable of measurement can be realized by winding a magnetizing coil around the cable and causing current to flow through the magnetizing coil.

The present invention is also applicable to a case where the object cable of measurement is coated or covered with a non-magnetic material (concrete, synthetic resin), etc.. The method according to the present invention is rather effective in a case where the object cable of measurement is coated or covered because the state of the cable therein cannot be viewed by eyes.

An apparatus for realizing a method of measuring the corrosion degree of a cable according to the present invention is constructed as follows.

Specifically, an apparatus for measuring the corrosion degree according to the present invention comprises a magnetizing coil for magnetizing an object cable of measurement whose corrosion degree is to be measured, a magnetic field measuring device for detecting strength of a magnetic field formed by the magnetizing coil, a magnetic flux measuring device for detecting an amount of magnetic flux passing through the object cable of measurement which is magnetized by the magnetizing coil, cross-sectional area calculating means for calculating a value relating to a cross-sectional area of the object cable of measurement on the basis of the magnetic field strength detected by the magnetic field measuring device, the amount of magnetic flux detected by the magnetic flux measuring device, and permeability of the object cable of measurement, and means for producing an output signal representing a degree of corrosion of the object cable of measurement on the basis of comparison between the value relating to the cross-sectional area calculated by the cross-sectional area calculating means and a value relating to a cross-sectional area of a reference cable.

When a human being compares the value relating to the cross-sectional area of the object cable of measurement and the cross-sectional area of the reference cable, the output signal producing means is not necessary.

Furthermore, if a human being calculates the value relating to the cross-sectional area of the object cable of measurement, the cross-sectional area calculating means is unnecessary.

According to the present invention, the magnetizing coil is wound around the object cable of measurement, and the current is caused to flow through the magnetizing coil, to magnetize the cable, whereby the size of the apparatus is reduced and the apparatus is made lightweight, resulting in good workability.

Furthermore, the degree of corrosion of the object cable of measurement is measured on the basis of the strength of the magnetic field for magnetizing the cable and the amount of magnetic flux passing through the magnetized cable, whereby high precision can be always maintained without depending on the measuring environment.

The present invention further provides a magnetizer suitable for magnetization of an object whose corrosion degree is to be evaluated.

The magnetizer comprises a reel to be arranged so as to enclose a part of an object of measurement and separable into a plurality of portions, means for coupling the plurality of portions of the reel to each other, and a magnetizing coil to be wound around the reel.

The reel comprises a plurality of portions. When these portions are so arranged as to enclose the object of measurement and are coupled to each other, the reel can be mounted on the object of measurement. When the magnetizing coil is wound around the reel, the magnetizer is completed.

Preferably, the magnetizer is fixed to the object of measurement using a fixing band. If a part of the fixing band enters a center hole of the reel in the magnetizer, the magnetizer is rotatably supported by the fixing band. Consequently, work for winding the magnetizing coil around the reel is facilitated.

The present invention further provides a detecting coil device used as a part of the magnetic flux measuring device.

The detecting coil device comprises a bobbin to be arranged so as to enclose a part of an object of measurement, and a detecting coil to be provided in a state where it is wound around the bobbin. The bobbin is so constructed as to be separable into a plurality of portions. The detecting coil comprises coil portions respectively provided in the plurality of separable portions of the bobbin and connectors connected to both ends of the coil portions. The corresponding connectors in the bobbin portions are coupled to each other when the bobbin portions are so coupled to each other as to form the bobbin, and the coil portions connected to each other form the detecting coil.

The detecting coil can be thus easily arranged around the object of measurement.

If a magnetic field detecting element constituting a part of the magnetic field measuring device is provided in the bobbin of the detecting coil device, the construction of the detecting coil device is made more compact.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 5a is an enlarged front view of a detecting coil device, FIG. 5b is a side view thereof, and FIG. 5c is a cross-sectional view taken along a line VC—VC shown in FIG. 5a;

FIG. 6a to FIG. 6c illustrate a bobbin in a detecting coil device in an enlarged manner, where FIG. 6a is a front view, FIG. 6b is a side view, and FIG. 6c is a bottom view;

FIG. 7b is a cross-sectional view taken along a line VIIB—VIIB shown in FIG. 7a; and FIG. 8a is a front view of a fixing band, FIG. 8b is a cross-sectional view taken along a line VIIIB—VIIIB shown in FIG. 8a, and FIG. 8c is a cross-sectional view taken along a line VIIIC—VIIIC shown in FIG. 8a.

DESCRIPTION OF THE PREFERRED EMBODIMENTS

Figure 1:
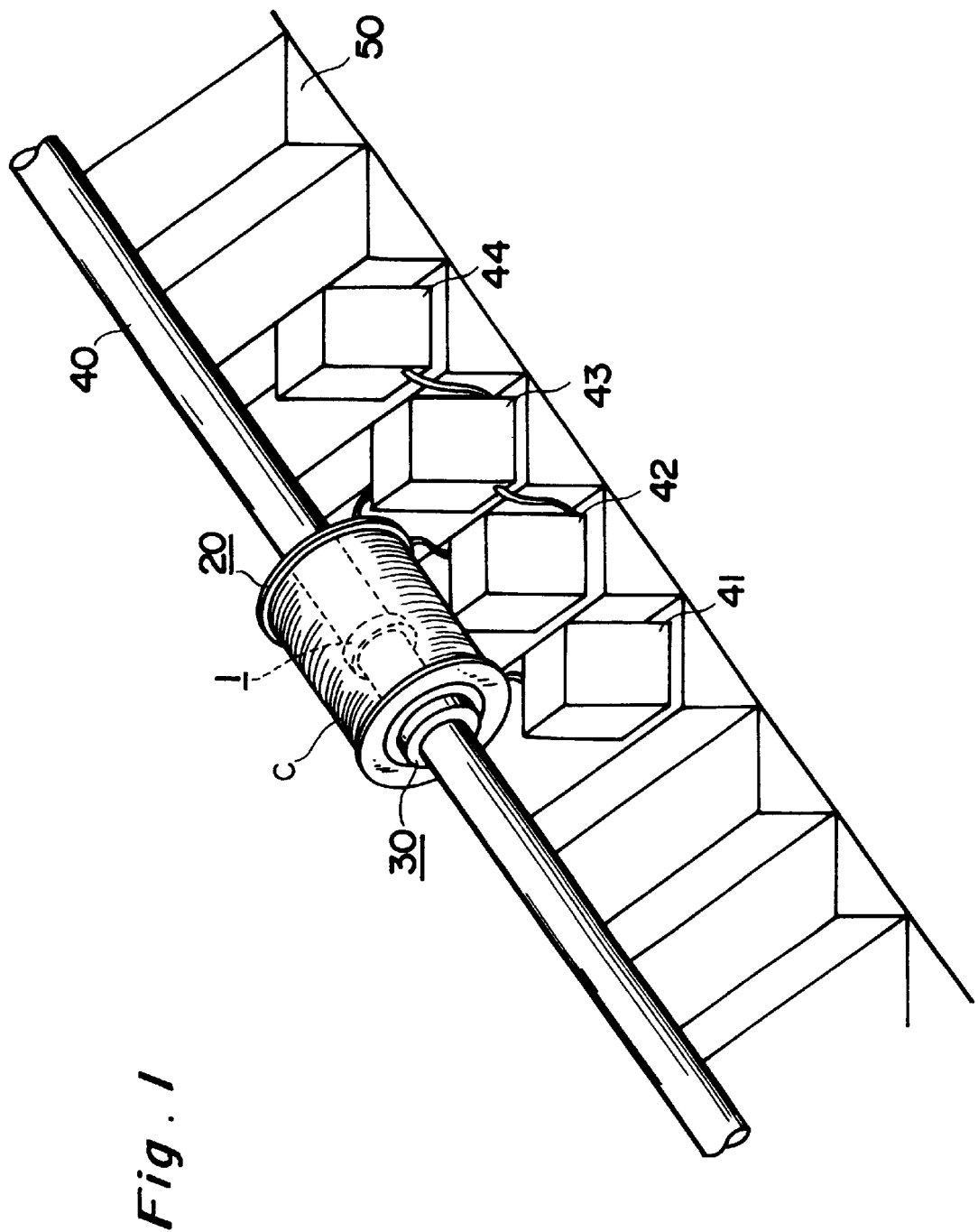
FIG. 1 is a perspective view showing the whole of an apparatus for measuring the corrosion degree of a cable.
Figure 2:
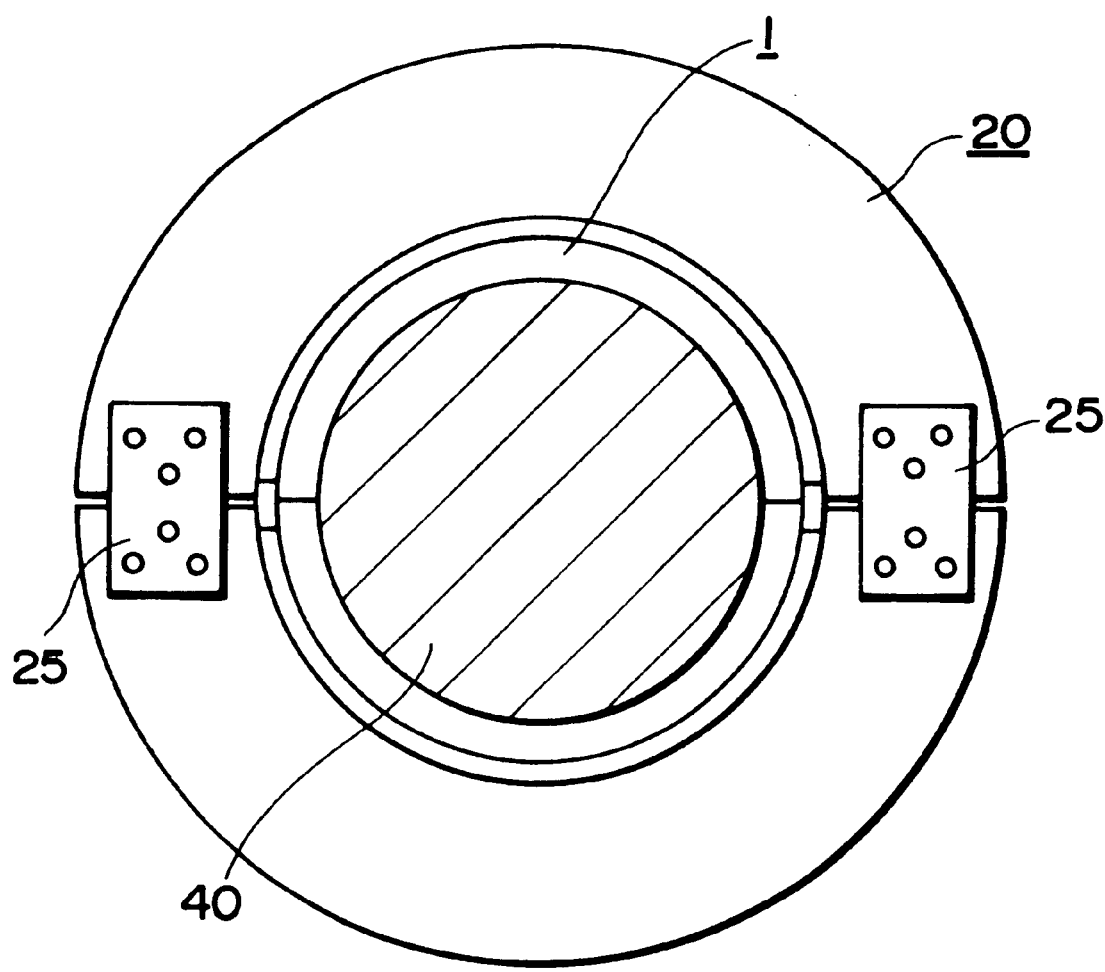
FIG. 2 is a front view showing the relationship between a magnetizer and a detecting coil device.
Figure 3:
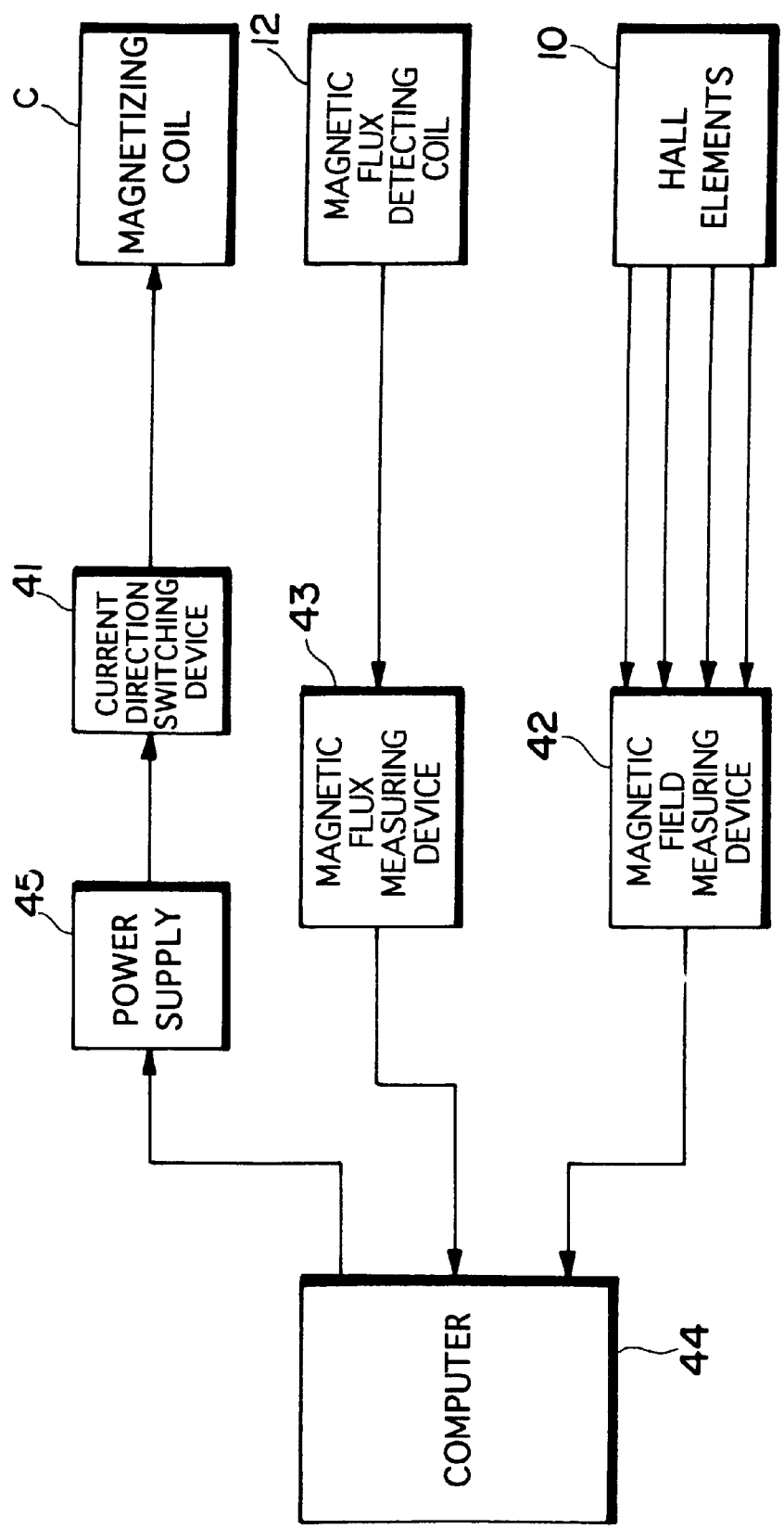
FIG. 3 is a block diagram showing the electrical construction of the apparatus for measuring the corrosion degree of a cable.

FIG. 1 is a perspective view of an apparatus for detecting the corrosion degree of a cable (a cable-corrosion-degree detecting apparatus), and FIG. 2 is a front view showing a state in which a detecting coil device 1 and a magnetizer 20 which constitute the cable-corrosion-degree detecting apparatus are mounted on the cable. FIG. 3 is a block diagram showing the electrical construction of the cable-corrosion-degree detecting apparatus.

A suspension bridge is taken as an example. In many cases, a working passage for maintaining and inspecting a cable 40 which suspends the bridge is provided along near the cable 40. The working passage is formed in the shape of a staircase in a place where the cable 40 is inclined (a step 50).

A magnetizer 20 is provided in a portion, which is to be inspected for corrosion, of the cable 40. The magnetizer 20 is fixed, to be positioned, to the cable 40 by fixing bands 30 fixed to the cable 40 on both sides of the magnetizer (only the front fixing band 30 is seen in FIG. 1, while the illustration of the fixing bands 30 is omitted in FIG. 2). There is a space between the inside of the magnetizer 20 and the cable 40. The detecting coil device 1 is provided in the space. The detecting coil device 1 is firmly fitted on the cable 40.

The magnetizer 20 includes a magnetizing coil C wound around the cable 40. Magnetizing current is caused to flow through the magnetizing coil C by a power supply 45 through a current direction switching device (switching device) 41 which is placed on the step 50. The direction of the current flowing through the magnetizing coil C is switched by the switching device 41 which is manually operated. A magnetic field is generated by causing the magnetizing current to flow through the magnetizing coil C, so that a portion, which is enclosed by the magnetizer 20, of the cable 40 is magnetized. The magnitude of the current flowing through the magnetizing coil C from the power supply 45 is controlled by a computer 44. The switching of the direction of the current may be also controlled by the computer 44. On the contrary, the magnitude of the current caused to flow through the magnetizing coil C may be manually adjusted.

The detecting coil device 1 includes a magnetic flux detecting coil 12 wound around the cable 40. The detecting coil 12 is connected to a magnetic flux measuring device (a flux meter) 43 by a shield line. The amount of magnetic flux passing through the cable 40 magnetized by the magnetizing coil C is detected by the magnetic flux measuring device 43, and its detection signal is fed to the computer 44.

The detecting coil device 1 is further provided with four Hall elements 10. The Hall elements (Hall effect devices) 10 are connected to a magnetic field measuring device (a Gauss meter) 42. The strength of the magnetic field in the vicinity of the cable 40 to which the magnetizer 20 is fixed, that is, the strength of the magnetic field generated by the magnetizer 20 is detected by the magnetic field measuring device 42 on the basis of the average value of Hall voltages respectively outputted from the four Hall elements 10, and is given to the computer 44.

The cross-sectional area (the reference cross-sectional area) $A_0$ of a new cable having the same permeability $\mu$ as that of the cable 40, composed of the same material as that of the cable 40, and of the same construction and size as those of the cable 40 is previously entered into the computer 44, and is stored in a memory of the computer 44. The reference cross-sectional area $A_0$ is previously measured with respect to the new cable in the same method as a method of measuring the cross-sectional area A of the cable 40 preferably using the corrosion degree detecting apparatus shown in FIGS. 1 to 3.

In the above-mentioned equation (2), the magnetic field strength H and the amount of magnetic flux (1) are respectively measured by the magnetic field measuring device 42 and the magnetic flux measuring device 43, and are fed to the computer 44. The computer 44 calculates the cross-sectional area A of a portion, on which the magnetizer 20 is mounted, of the cable 40 on the basis of the equation (2) using the magnetic field strength H and the amount of magnetic flux $\Phi$ which are given and the permeability $\mu$ previously set (a magnetic field strength of more than approximately 40 KA/m is required in order to consider the permeability to be constant). Further, the computer 44 calculates the corrosion degree of the cable in accordance with the following equation using the calculated cross-sectional area A and the reference cross-sectional area $A_0$ previously set in the computer 44.

$$\text{Corrosion degree} = A/A_0 (\%) \quad (3)$$

The cable 40 is a ferromagnetic material, and its component is mainly iron (Fe). From the fact that a part of the cable 40 is corroded, it is considered that the iron component is changed into iron oxide ($Fe_2O_3$) by oxidation. Iron oxide may be treated as a non-magnetic material because the permeability thereof is small.

When a part of the cable 40 is corroded, the cross-sectional area A of a portion which is a ferromagnetic material is decreased depending on the degree of corrosion. Using the cross-sectional area $A_0$ of the reference cable as a basis, if comparison between the reference cross-sectional area $A_0$ and the measured cross-sectional area A is made, then the degree of corrosion of the cable 40 is found. The corrosion degree can be also defined by the following equation in place of the equation (3):

$$\text{Corrosion degree} = (A_0 - A)A_0 \quad (4)$$

Alternatively, the other definition can be also used, (it is sufficient that $A_0$ and A can be compared with each other).

Figure 4:
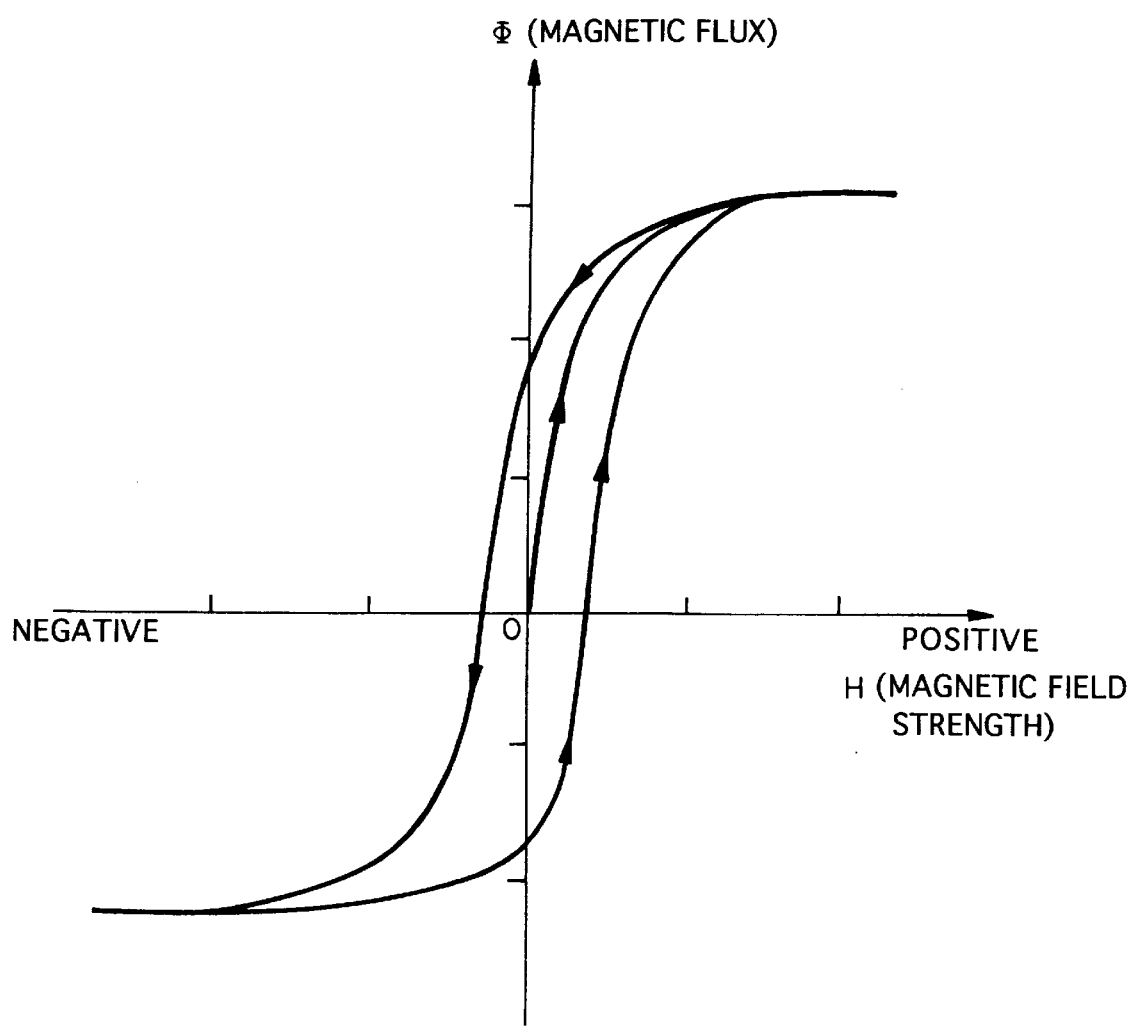
FIG. 4 is a graph showing a magnetization curve indicating hysteresis characteristics.

FIG. 4 shows the relationship between the strength H of a magnetic field to magnetize a ferromagnetic material and the amount of magnetic flux generated in the ferromagnetic material, that is, hysteresis characteristics. There is a region where the amount of magnetic flux ( is not uniquely determined with respect to the strength H of the magnetic field due to the hysteresis characteristics. In the above-mentioned measurements of the corrosion degree, the cross-sectional area A of the cable 40 is calculated from the relationship between the magnetic field strength H and the amount of magnetic flux $\Phi$ in a region where the amount of magnetic flux $\Phi$ is saturated.

More preferably, the cross-sectional area A or the corrosion degree is calculated on the basis of the average value of measured values at a plurality of points on a magnetization curve, as described below.

The magnetizing current caused to flow through the magnetizing coil C is gradually increased from 0 [A] until the magnetic flux is saturated (to 500 [A], for example). The magnetic field strength $H_1$ and the amount of magnetic flux $\Phi_1$ in a case where the magnetic flux is saturated are respectively measured by the magnetic field measuring device 42 and the magnetic flux measuring device 43. The cross-sectional area $A_1$ for the first time is calculated in accordance with the equation (2) using the magnetic field strength $H_1$ and the amount of magnetic flux $\Phi_1$ which are measured and the permeability $\mu$ of the cable 40.

The magnetizing current is then gradually decreased, and is returned to 0 [A] once. The current direction switching device 41 is operated, to switch the direction in which the magnetizing current flows. The magnetizing current is gradually increased in a negative direction. When the magnetic flux is saturated (for example, when magnetizing current of –500 [A] flows), the magnetic field strength $H_2$ and the amount of magnetic flux $\Phi_2$ are respectively measured by the magnetic field measuring device 42 and the magnetic flux measuring device 43. The cross-sectional area $A_2$ for the second time is calculated from the equation (2) using the magnetic field strength $H_2$ and the amount of magnetic flux $\Phi_2$ which are measured and the permeability $\mu$ of the cable 40.

Furthermore, the magnetizing current is gradually increased in a positive direction from –500 [A], and is returned to 0 [A] once. The current direction switching device 41 is so operated that the direction of the magnetizing current is reversed again, after which the magnetizing current is gradually increased in a positive direction to 500 [A] again. The magnetic field strength $H_3$ and the amount of magnetic flux $\Phi_3$ at that time are measured. The cross-sectional area $A_3$ for the third time is calculated from the equation (2) using the magnetic field strength $H_3$ and the amount of magnetic flux $\Phi_3$ which are measured and the permeability $\mu$ of the cable 40.

The magnetizing current is gradually decreased from 500 [A] again. When the magnetizing current is 0 [A], the current direction switching device 41 is operated, to reverse the direction of the magnetizing current. The magnetizing current is further gradually decreased. When the magnetizing current is –500 [A] again, the magnetic field strength $H_4$ and the amount of magnetic flux $\Phi_4$ are measured. The cross-sectional area $A_4$ for the fourth time is calculated from the equation (2) using the magnetic field strength $H_4$ and the amount of magnetic flux $\Phi_4$ which are measured and the permeability $\mu$ of the cable 40.

The average cross-sectional area $A_{AV}$ of the cross-sectional area $A_1$ for the first time to the cross-sectional area $A_4$ for the fourth time which are obtained in the above-mentioned manner is calculated. The corrosion degree is obtained from the ratio of the calculated average cross-sectional area $A_{AV}$ to the reference cross-sectional area $A_0$ (if the equation (3) is used, the corrosion degree=$A_{AV}/A_0$).

The average value $H_{AV}$ of the magnetic field strength $H_1$ to the magnetic field strength $H_4$ which are respectively obtained for the first time to the fourth time is calculated, and the average value $\Phi_{AV}$ of the amount of magnetic flux $\Phi_1$ for the first time to the amount of magnetic flux $\Phi_4$ for the fourth time is calculated. The average cross-sectional area $A_{AV}$ may be found using the average values $H_{AV}$ and $\Phi_{AV}$.

The number of times of the measurements of the magnetic field strength and the amount of the magnetic flux is not limited to four as described above. It goes without saying that it may be 2, 3 or 5 or more.

With respect to the long cable 40, the degree of corrosion of the entire length of the cable 40 can be evaluated, by repeating the above-mentioned measurements while gradually changing the positions where the magnetizer 20 and the detecting coil device 1 are attached (by a length nearly corresponding to the length of the magnetizer 20).

When the cable 40 is not bare but is covered with any non-magnetic material (for example, concrete), the above-mentioned measuring method can be also used. In this case, the magnetizer 20 and the detecting coil device 1 may be so provided as to enclose the whole of the non-magnetic material with which the cable 40 is coated. When the cable is coated, the degree of corrosion of the cable cannot be viewed, so that the above-mentioned method is particularly effective.

Although in the foregoing, the measured cross-sectional area A and the reference cross-sectional area $A_0$ are arithmetically compared with each other, to find the corrosion degree, there are various methods of finding the corrosion degree. For example, if a calibration curve is previously drawn on paper respectively taking the cross-sectional area A and the corrosion degree along the abscissa and the ordinate (or is stored in the memory of the computer 44), the corrosion degree can be obtained from the measured cross-sectional area A utilizing the calibration curve. Not the cross-sectional areas A and $A_0$ themselves but values proportional thereto can be also used. Further, if all the measurements are made with the magnetic field strength H being kept constant, the degree of corrosion can be known directly (without calculating the cross-sectional area) from the measured amount of magnetic flux $\Phi$.

FIGS. 5a to 5c illustrate the detecting coil device 1 in a slightly enlarged manner, where FIG. 5a is a front view, FIG. 5b is a side view, and FIG. 5c is a cross-sectional view taken along a line VC—VC shown in FIG. 5a. FIGS. 6a to 6c illustrate a bobbin constituting the detecting coil device 1 in a further enlarged manner, where FIG. 6a is a front view, FIG. 6b is a side view, and FIG. 6c is a bottom view.

The detecting coil device 1 has an annular shape as a whole, and comprises two half members 3 and 4 in a shape obtained by just halving the annular shape. The half members 3 and 4 are formed of a non-magnetic and insulating material such as synthetic resin. The inside diameter of the detecting coil device 1 is made approximately the same as the outside diameter of the cable 40 (or a material covering the cable).

The half member 3 includes a semicircular bobbin 2. Flanges 2a are formed on both sides of the semicircular bobbin 2, and several coil portions 12 are mounted in a mutually insulated state on an outer peripheral surface of the bobbin 2 between the flanges 2a. Connectors 13 are provided at both ends of the bobbin 2, and both ends of the coil portions 12 are respectively connected the connectors 13.

The half member 3 is provided with a semicircular outer cover 6 which is a little larger than the bobbin 2 in diameter, and the bobbin 2 and the outer cover 6 are coupled to each other by side plates 11 on their side surfaces.

The half member 4 is of almost the same construction as that of the half member 3, and includes a semicircular bobbin 5 and an outer cover 7 which is larger than the semicircular bobbin 5 in size. Side plates 11 are attached on both side surfaces of the bobbin 5 and the outer cover 7. Several coil portions are provided on an outer peripheral surface of the bobbin 5, and are connected to connectors at both ends of the bobbin 5.

Four Hall elements 10 are provided at approximately 90° intervals in spaces inside the half members 3 and 4.

Connectors 9 are provided on the side plates 11 on one side surface of the detecting coil device 1. The Hall elements 10 are connected to the connectors 9. Shield lines 16 are connected to the connectors 9, so that output signals of the Hall elements 10 are led outward, and are fed to the magnetic field measuring device 42. A connector 8 is also provided on the side surface of the detecting coil device 1. The coil portions 12 are connected to the connector 8. A shield line 15 is connected to the connector 8, so that a detecting coil (formed of the coil portions 12) is connected to the magnetic flux measuring device 43.

Catch grips 14 which are paired are mounted on ends of the half members 3 and 4 of the detecting coil device 1. The half member 3 and the half member 4 are separably coupled to each other by the catch grips 14, to constitute the detecting coil device 1.

In the execution of the work for measuring the corrosion degree of the cable 40, the catch grips 14 are opened, whereby the detecting coil device 1 is divided into the half members 3 and 4. The cable 40 (or the covering member on the cable when the cable is covered) is interposed between the two half members 3 and 4. The annular detecting coil device 1 is formed by closing the catch grips 14, and is firmly fixed to the cable 40. The connectors 13 provided in the half member 3 and the connectors (not shown) provided in the half member 4 are electrically connected to each other, so that the coil portions 12 provided in the half member 3 and the coil portions (not shown) provided in the half member 4 are so electrically connected to each other as to be wound around the cable 40 (by several turns), whereby the detecting coil is formed.

The shield line 15 is connected to the connector 8, so that the detecting coil is connected to the magnetic flux measuring device 43. Similarly, the shield lines 16 are connected to the connectors 9, so that the Hall elements 10 are connected to the magnetic field measuring device 42.

Figure 7B:
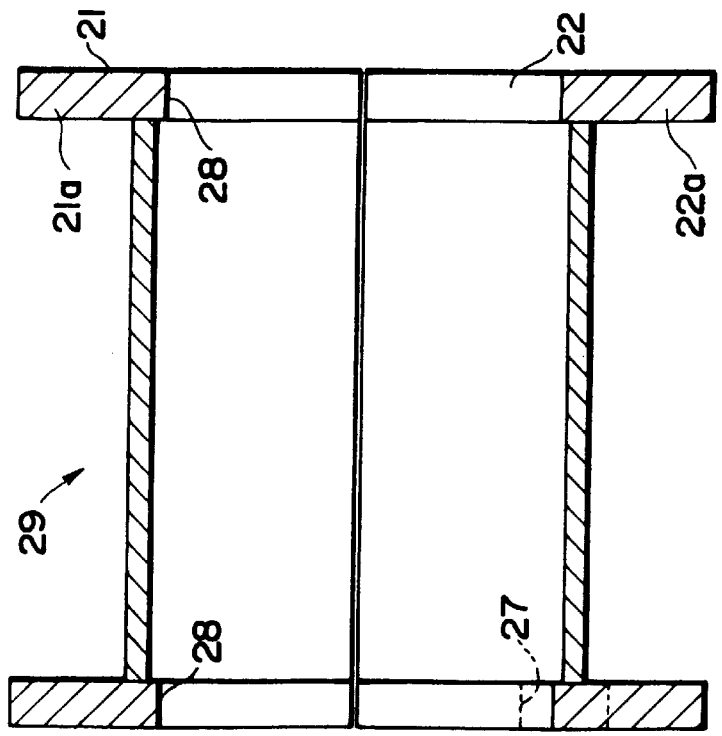
Figure 7A:
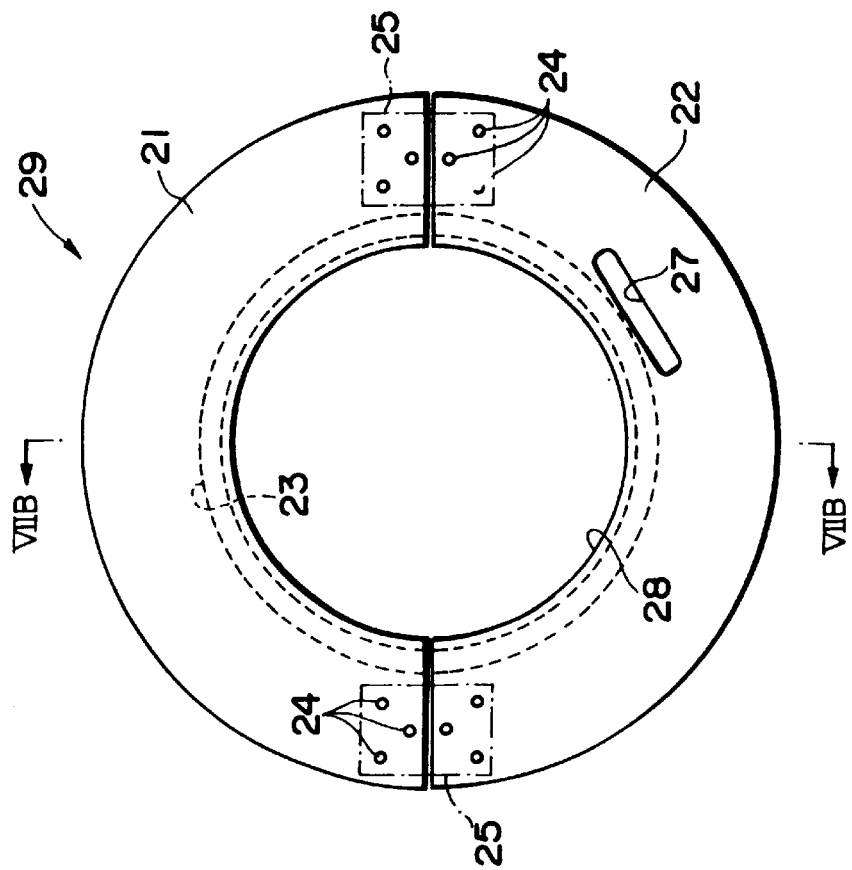
FIG. 7a is a front view of a reel constituting a magnetizer.

FIGS. 7*a* and 7*b* illustrate a reel 29 included in the magnetizer 20, where FIG. 7*a* is a front view, and FIG. 7*b* is a cross-sectional view taken along a line VIIB—VIIB shown in FIG. 7*a*.

The magnetizer 20 is constructed by winding the magnetizing coil C around the reel 29. The reel 29 is formed of a non-magnetic material, for example, aluminum.

The reel 29 comprises two semicylinders 21 and 22. Flanges 21*a* are formed at both ends of the semicylinder 21, and flanges 22*a* are formed at both ends of the semicylinder 22. A plurality of screw holes 24 are formed in a joint portion of the flanges 21*a* and 22*a*. An opening 27 for drawing ends of a coil from inside of the reel 29 is formed in the flange 22*a* of the semicylinder 22.

The semicylinder 21 and the semicylinder 22 are so butted together as to constitute a cylinder, and plates 25 are placed in respective joint portions of the flanges 21*a* at both ends of the semicylinder 21 and of the flanges 22*a* at both ends of the semicylinder 22. The plate 25 is screwed on the flanges 21*a* and 22*a* through the screw holes 24, so that the semicylinder 21 and the semicylinder 22 are coupled to each other to be a cylinder (reel). The inside diameter of this cylinder (reel) is so made large enough to contain inside thereof the cylinder of the above-mentioned detecting coil device 1.

In the work for measuring the corrosion degree of the cable 40, the detecting coil device 1 is first mounted on the cable 40 as described above. The cable 40 and the detecting coil device 1 mounted thereon are covered with the semicylinders 21 and 22 so as to be enclosed thereby, and the semicylinders 21 and 22 are coupled to each other by screwing, to form the reel 29. The reel 29 is fixed by the fixing band 30 as described later. The detecting coil C is manually wound around the reel 29. The detecting coil C is in regular or normal winding in order to uniformly magnetize the cable 40. For example, the detecting coil C is wound into four layers with 25 turns per layer. Both ends of the magnetizing coil C are pulled out of the opening 27, and are connected to the current direction switching device 41. By the foregoing, the magnetizer 20 is constructed. The magnetizing coil C may be mechanically wound using a motor or the like.

Considering the workability, it is preferable that the number of turns of the magnetizing coil C is reduced (for example, 50~500 turns), and a large magnetizing current flows through the magnetizing coil C.

FIGS. 8*a*, 8*b* and 8*c* illustrate a fixing band, where FIG. 8*a* is a front view, FIG. 8*b* is a cross-sectional view taken along a line VIIIB—VIIIB shown in FIG. 8*a*, and FIG. 8*c* is a cross-sectional view taken along a line VIIIC—VIIIC shown in FIG. 8*a*.

A fixing band 30 comprises semicircular half members 31 and 32. The fixing band 30 is also formed of a non-magnetic material.

Fixing pieces 33 are formed at both ends of each of the half members 31 and 32 in its radial direction. Screw holes 34 are formed in the fixing pieces 33. The half members 31 and 32 are so butted together as to constitute a circle, and are coupled to each other by screwing, through the screw holes 34, the fixing pieces 33 of the half members 31 and 32 which are brought into contact with each other.

Rubber packings 35 are attached along inner peripheral surfaces of the half members 31 and 32. The inside diameter of the fixing band 30 is made approximately the same as the outside diameter of the cable 40 (or the cover member on the cable 40). An inner peripheral surface of the fixing band 30 and an outer peripheral surface of the cable 40 are tightly made contact with each other by the rubber packings 35.

A flange 36 extending outward is formed in positions slightly inside the outer peripheral surfaces of the half members 31 and 32. When the fixing band 30 is so mounted on the cable 40 that the fixing band 30 loosely enters a center hole 28 of the flanges 21*a* and 22*a* of the reel 29 in the magnetizer 20, and the flange 36 is brought into contact with the flanges 21*a* and 22*a*, the reel 29 is rotatably held by the fixing band 30. Coil winding work can be made easy by rotating the reel 29 when the detecting coil C is wound.

The fixing band 30 need not be necessarily provided on both sides of the magnetizer 20. When the cable 40 is inclined as shown in FIG. 1, the fixing band 30 may be mounted only on the lower side of the magnetizer 20. Unless the cable 40 is inclined, the fixing band 30 is not necessarily required.

As many apparently widely different embodiments of the present invention can be made without departing from the spirit and scope thereof, it is to be understood that the invention is not limited to the specific embodiments thereof except as defined in the appended claims.

What is claimed is:

1. An apparatus for measuring a degree of corrosion of a cable, comprising a magnetizing coil magnetizing an object cable whose degree of corrosion is to be measured, and a magnetic flux detecting coil detecting an amount of magnetic flux passing through the object cable which is magnetized by said magnetizing coil, wherein a degree of corrosion of the object cable is determined based on the amount of magnetic flux detected by said magnetic flux detecting coil, said apparatus further comprising:

a magnetizer having a reel to be arranged so as to enclose a part of the object cable and separable into a plurality of reel portions, and means for coupling the plurality of reel portions to each other, wherein there is a space between an inside of said reel of said magnetizer and the object cable said reel of said magnetizer is rotatable with respect to the object cable, and said magnetizing coil is to be wound around said reel of said magnetizer; and a detecting coil device having a bobbin to be arranged so as to enclose the part of the object cable and separable into a plurality of bobbin portions, wherein said detecting coil device is provided around said bobbin, and said detecting coil device is to be disposed in said space inside said reel of said magnetizer so as to be fitted on the object cable.

2. The apparatus according to claim 1, further comprising a band to fix said magnetizer on the object cable, wherein said fixing band is separable into a plurality of fixing band portions, and said fixing band comprises means for coupling the plurality of fixing band portions to each other, and a flange protruding outward.

3. The apparatus according to claim 1, further comprising a magnetic field detecting element provided inside said bobbin in said detecting coil device.

4. The apparatus according to claim 1, wherein in said detecting coil device, said detecting coil comprises a plurality of coil portions provided in the plurality of bobbin portions and a plurality of connectors connected to both ends of the plurality of coil portions, the corresponding plurality of connectors in the plurality of bobbin portions being coupled to each other when the plurality of bobbin portions are so coupled to each other as to form the bobbin, thereby the plurality of coil portions connected to each other form said detecting coil.

5. The apparatus according to claim 1, further comprising a magnetic flux measuring device, which includes said detecting coil device, measuring the amount of magnetic flux passing through the object cable.

6. The apparatus according to claim 5, further comprising a magnetic field measuring device measuring a strength of a magnetic field formed by said magnetizing coil based on a signal from a magnetic field detecting element provided inside said bobbin in said detecting coil device.

7. The apparatus according to claim 6, further comprising cross-sectional area calculating means for calculating a value relating to a cross-sectional area of the object cable based on the strength of the magnetic field measured by the magnetic field measuring device, the amount of magnetic flux measured by said magnetic flux measuring device, and permeability of the object cable.

8. The apparatus according to claim 7, further comprising means for producing an output signal representing a degree of corrosion of the object cable based on a comparison between the value relating to the cross-sectional area calculated by said cross-sectional area calculating means and a value relating to a cross-sectional area of a reference cable.

9. A method of measuring a degree of corrosion of an object cable using the apparatus according to claim 1, comprising:

magnetizing, using said magnetizing coil, the object cable whose degree of corrosion is to be measured;

detecting, using said magnetic flux detecting coil, an amount of magnetic flux passing through the magnetized object cable; and measuring the degree of corrosion of the object cable based on the detected amount of magnetic flux.

10. A method of measuring a degree of corrosion of an object cable using the apparatus according to claim 3, comprising:

magnetizing, using said magnetizing coil, the object cable whose degree of corrosion is to be measured;

detecting, using said magnetic field detecting element, a strength of a magnetic field for magnetizing the object cable;

detecting, using said magnetic flux detecting coil, an amount of magnetic flux passing through the magnetized object cable; and measuring the degree of corrosion of the object cable based on the detected strength of the magnetic field and the detected amount of magnetic flux.

11. A method of measuring a degree of corrosion of an object cable using the apparatus according to claim 3, comprising:

magnetizing, using said magnetizing coil, the object cable whose degree of corrosion is to be measured;

detecting, using said magnetic field detecting element, a strength of a magnetic field for magnetizing the object cable;

detecting, using said magnetic flux detecting coil, an amount of magnetic flux passing through the magnetized object cable;

calculating a value relating to a cross-sectional area of the object cable based on the detected magnetic field strength, the detected amount of magnetic flux, and permeability of the object cable; and measuring the degree of corrosion of the object cable based on a comparison between the calculated value relating to the cross-sectional area of the object cable and a value relating to a cross-sectional area of a reference cable.

\* \* \* \* \*